(12) United States Patent
Roessig et al.

(10) Patent No.: US 11,472,860 B2
(45) Date of Patent: Oct. 18, 2022

(54) CHIMERIC ANTIGEN RECEPTORS

(71) Applicants: Westfaelische-Wilhelms-Universitaet Muenster, Muenster (DE); Heinrich-Heine-Universitaet Duesseldorf, Duesseldorf (DE)

(72) Inventors: Claudia Roessig, Muenster (DE); Helmut Hanenberg, Krefeld (DE); Constanze Wiek, Mettmann (DE); Tabea Ibach, Duesseldorf (DE); Katharina Roellecke, Duesseldorf (DE)

(73) Assignees: WESTFAELISCH-WILHELMS-UN-IVERSITAET, Muenster (DE); HEINRICH-HEINE-UNIVERSITAET DUSSELFDORF, Dusselfdorf (DE)

( * ) Notice: Subject to any disclaimer, the term of this patent is extended or adjusted under 35 U.S.C. 154(b) by 0 days.

(21) Appl. No.: 15/697,717

(22) Filed: Sep. 7, 2017

(65) Prior Publication Data
US 2018/0094044 A1 Apr. 5, 2018

(30) Foreign Application Priority Data
Sep. 8, 2016 (EP) .................................. 16187740

(51) Int. Cl.
| | |
|---|---|
| C07K 14/705 | (2006.01) |
| C07K 14/735 | (2006.01) |
| A61P 35/02 | (2006.01) |
| C07K 14/725 | (2006.01) |
| C07K 16/28 | (2006.01) |

(52) U.S. Cl.
CPC ........ *C07K 14/70596* (2013.01); *A61P 35/02* (2018.01); *C07K 14/7051* (2013.01); *C07K 14/70517* (2013.01); *C07K 14/70521* (2013.01); *C07K 14/70535* (2013.01); *C07K 14/70578* (2013.01); *C07K 16/2878* (2013.01); *C07K 16/2896* (2013.01); *C07K 2317/53* (2013.01); *C07K 2317/622* (2013.01); *C07K 2319/00* (2013.01); *C07K 2319/02* (2013.01); *C07K 2319/03* (2013.01)

(58) Field of Classification Search
CPC ......... C07K 14/705–70535; C07K 16/00–468; C07K 2319/00–03
See application file for complete search history.

(56) References Cited

U.S. PATENT DOCUMENTS

| | | | | |
|---|---|---|---|---|
| 2015/0093401 A1* | 4/2015 | Pule | .................... | C07K 16/2887 |
| | | | | 424/185.1 |
| 2016/0046700 A1* | 2/2016 | Foster | .................... | A61K 35/14 |
| | | | | 424/134.1 |

FOREIGN PATENT DOCUMENTS

| | | | | |
|---|---|---|---|---|
| WO | WO-2015150771 A1 * | 10/2015 | ........... | C12N 5/0636 |
| WO | 2016/042461 A1 | 3/2016 | | |

OTHER PUBLICATIONS

Fehse et al., Gene Therapy 9:1633-38 (Year: 2002).*
Rischer et al. Br. J. Haematol 126:583-592 (Year: 2004).*
Philip et al., Blood 124:1277-87 (Year: 2014).*
Kofler et al., Mol Ther 19:760-767 (Year: 2011).*
S S Kenderian et al., "CD33-specific chimeric antigen receptor T cells exhibit potent preclinical activity against human acute myeloid leukemia", Leukemia., vol. 29, No. 88, May 22, 2015, pp. 1637-1647.
Michael C. Jensen et al., "Designing chimeric antigen receptors to effectively and safely target tumors", Current Opinion in Immunology, vol. 33, Jan. 23, 2015, pp. 9-15.
Albert T. Gacerez et al., "How Chimeric Antigen Receptor Design Affects Adoptive T Cell Therapy", Journal of Cellular Physiology, vol. 231, No. 12, Jun. 2, 2016, pp. 2590-2598.
K Roellecke et al., "Optimized human CYP4B1 in combination with the alkylator prodrug 4-ipomeanol serves as a novel suicide gene system for adoptive T-cell therapies", Gene Therapy, vol. 23, No. 7, Jul. 1, 2016, pp. 615-626.

* cited by examiner

*Primary Examiner* — Jessica H Roark
(74) *Attorney, Agent, or Firm* — WCF IP

(57) ABSTRACT

In a first aspect, provided herein are chimeric antigen receptors (CAR) composed of at least an extracellular domain, a transmembrane domain and an intracellular domain, the extracellular domain comprises a spacer domain located C-terminally to a ligand-binding-domain also present in the extracellular domain, whereby the spacer domain comprises at least part of the CD34 molecule. Also provided are nucleic acid molecules encoding the same as well as vectors and cells containing the same. The cells include engineered T-cells and NK-cells and derivatives thereof. A pharmaceutical composition comprising the CAR e.g. in form of a vector, a polynucleotide encoding the CAR or the CAR itself and, in addition, cells, cell lines or host cells accordingly are provided. The CAR is useful in adoptive cell therapy. Finally, a method for enrichment or purification of CAR, in particular, of genetically engineered cells, cell lines or host cells expressing the CAR is provided.

20 Claims, 6 Drawing Sheets

Specification includes a Sequence Listing.

SEQUENCE LISTING

```
<160> NUMBER OF SEQ ID NOS: 14

<210> SEQ ID NO 1
<211> LENGTH: 987
<212> TYPE: DNA
<213> ORGANISM: artificial sequence
<220> FEATURE:
<223> OTHER INFORMATION: codon optimized CD34 encoding nucleic acid
      sequence
```

```
<220> FEATURE:
<221> NAME/KEY: CDS
<222> LOCATION: (1)..(987)

<400> SEQUENCE: 1 atg ctc gtg cgg aga ggc gct aga gcc ggc cct aga atg cct aga gga       48
Met Leu Val Arg Arg Gly Ala Arg Ala Gly Pro Arg Met Pro Arg Gly
1               5                   10                  15 tgg acc gcc ctg tgc ctg ctg agc ctg ctg cct agc ggc ttc atg agc       96
Trp Thr Ala Leu Cys Leu Leu Ser Leu Leu Pro Ser Gly Phe Met Ser
            20                  25                  30 ctg gac aac aac ggc acc gcc acc cct gag ctg cct acc cag ggc acc      144
Leu Asp Asn Asn Gly Thr Ala Thr Pro Glu Leu Pro Thr Gln Gly Thr
        35                  40                  45 ttc agc aac gtg tcc acc aat gtg tcc tac cag gaa acc acc acc ccc      192
Phe Ser Asn Val Ser Thr Asn Val Ser Tyr Gln Glu Thr Thr Thr Pro
    50                  55                  60 agc acc ctg ggc agc aca tct ctg cac cct gtg tcc cag cac ggc aac      240
Ser Thr Leu Gly Ser Thr Ser Leu His Pro Val Ser Gln His Gly Asn
65                  70                  75                  80 gag gcc acc acc aac atc acc gag aca acc gtg aag ttc acc agc acc      288
Glu Ala Thr Thr Asn Ile Thr Glu Thr Thr Val Lys Phe Thr Ser Thr
                85                  90                  95 agc gtg atc acc tcc gtg tac ggc aac acc aac agc agc gtg cag agc      336
Ser Val Ile Thr Ser Val Tyr Gly Asn Thr Asn Ser Ser Val Gln Ser
            100                 105                 110 cag acc tcc gtg atc agc acc gtg ttt acc acc ccc gct aat gtg tcc      384
Gln Thr Ser Val Ile Ser Thr Val Phe Thr Thr Pro Ala Asn Val Ser
        115                 120                 125 acc ccc gaa acc acc ctg aag ccc agc ctg tct ccc gga aac gtg tcc      432
Thr Pro Glu Thr Thr Leu Lys Pro Ser Leu Ser Pro Gly Asn Val Ser
    130                 135                 140 gac ctg agc acc acc tct acc agc ctg gcc acc agc ccc acc aag cct      480
Asp Leu Ser Thr Thr Ser Thr Ser Leu Ala Thr Ser Pro Thr Lys Pro
145                 150                 155                 160 tac aca agc agc agc ccc atc ctg agc gac atc aag gcc gag atc aag      528
Tyr Thr Ser Ser Ser Pro Ile Leu Ser Asp Ile Lys Ala Glu Ile Lys
                165                 170                 175 tgc agc ggc atc cgg gaa gtg aag ctg aca cag ggc atc tgc ctg gaa      576
Cys Ser Gly Ile Arg Glu Val Lys Leu Thr Gln Gly Ile Cys Leu Glu
            180                 185                 190 cag aac aag acc agc agc tgc gcc gag ttc aag aag gac aga ggc gag      624
Gln Asn Lys Thr Ser Ser Cys Ala Glu Phe Lys Lys Asp Arg Gly Glu
        195                 200                 205 ggc ctg gcc aga gtg ctg tgt ggc gaa gaa cag gcc gat gcc gat gct      672
Gly Leu Ala Arg Val Leu Cys Gly Glu Glu Gln Ala Asp Ala Asp Ala
    210                 215                 220 ggc gct caa gtg tgc tct ctg ctg gcc cag agc gaa gtg cgg cct          720
Gly Ala Gln Val Cys Ser Leu Leu Ala Gln Ser Glu Val Arg Pro
225                 230                 235                 240 cag tgc ctg ctg ctg gtg ctg gcc aac aga acc gag atc agc agc aaa      768
Gln Cys Leu Leu Leu Val Leu Ala Asn Arg Thr Glu Ile Ser Ser Lys
                245                 250                 255 ctg cag ctg atg aag aag cac cag agc gac ctg aag aag ctg ggc atc      816
Leu Gln Leu Met Lys Lys His Gln Ser Asp Leu Lys Lys Leu Gly Ile
            260                 265                 270 ctg gac ttc acc gag cag gac gtg gcc tcc cac cag agc tac agc cag      864
Leu Asp Phe Thr Glu Gln Asp Val Ala Ser His Gln Ser Tyr Ser Gln
        275                 280                 285 aaa acc ctg atc gcc ctc gtg acc tct ggc gcc ctg ctg gca gtg ctg      912
```

```
Lys Thr Leu Ile Ala Leu Val Thr Ser Gly Ala Leu Leu Ala Val Leu
            290                 295                 300 gga atc acc ggc tac ttt ctg atg aac cgg cgg agc tgg tcc ccc acc     960
Gly Ile Thr Gly Tyr Phe Leu Met Asn Arg Arg Ser Trp Ser Pro Thr
305                 310                 315                 320 ggc gaa aga ctg gaa ctg gaa ccc tag                                 987
Gly Glu Arg Leu Glu Leu Glu Pro
                325

<210> SEQ ID NO 2
<211> LENGTH: 328
<212> TYPE: PRT
<213> ORGANISM: artificial sequence
<220> FEATURE:
<223> OTHER INFORMATION: Synthetic Construct

<400> SEQUENCE: 2

Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
```

```
                305                 310                 315                 320
Gly Glu Arg Leu Glu Leu Glu Pro
            325

<210> SEQ ID NO 3
<211> LENGTH: 16
<212> TYPE: PRT
<213> ORGANISM: homo sapiens

<400> SEQUENCE: 3

Glu Leu Pro Thr Gln Gly Thr Phe Ser Asn Val Ser Thr Asn Val Ser
1               5                   10                  15

<210> SEQ ID NO 4
<211> LENGTH: 32
<212> TYPE: PRT
<213> ORGANISM: homo sapiens

<400> SEQUENCE: 4

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

<210> SEQ ID NO 5
<211> LENGTH: 49
<212> TYPE: PRT
<213> ORGANISM: homo sapiens

<400> SEQUENCE: 5

Glu Leu Pro Thr Gln Gly Thr Phe Ser Asn Val Ser Thr Asn Val Ser
1               5                   10                  15

Tyr Gln Glu Thr Thr Thr Pro Ser Thr Leu Gly Ser Thr Ser Leu His
            20                  25                  30

Pro Val Ser Gln His Gly Asn Glu Ala Thr Thr Asn Ile Thr Glu Thr
        35                  40                  45

Thr

<210> SEQ ID NO 6
<211> LENGTH: 59
<212> TYPE: PRT
<213> ORGANISM: homo sapiens

<400> SEQUENCE: 6

Ser Leu Asp Asn Asn Gly Thr Ala Thr Pro Glu Leu Pro Thr Gln Gly
1               5                   10                  15

Thr Phe Ser Asn Val Ser Thr Asn Val Ser Tyr Gln Glu Thr Thr Thr
            20                  25                  30

Pro Ser Thr Leu Gly Ser Thr Ser Leu His Pro Val Ser Gln His Gly
        35                  40                  45

Asn Glu Ala Thr Thr Asn Ile Thr Glu Thr Thr
    50                  55

<210> SEQ ID NO 7
<211> LENGTH: 69
<212> TYPE: PRT
<213> ORGANISM: homo sapiens

<400> SEQUENCE: 7

Glu Leu Pro Thr Gln Gly Thr Phe Ser Asn Val Ser Thr Asn Val Ser
1               5                   10                  15
```

```
Tyr Gln Glu Thr Thr Thr Pro Ser Thr Leu Gly Ser Thr Ser Leu His
            20                  25                  30

Pro Val Ser Gln His Gly Asn Glu Ala Thr Thr Asn Ile Thr Glu Thr
            35                  40                  45

Thr Val Lys Phe Thr Ser Thr Ser Val Ile Thr Ser Val Tyr Gly Asn
        50                  55                  60

Thr Asn Ser Ser Val
65

<210> SEQ ID NO 8
<211> LENGTH: 99
<212> TYPE: PRT
<213> ORGANISM: homo sapiens

<400> SEQUENCE: 8

Glu Leu Pro Thr Gln Gly Thr Phe Ser Asn Val Ser Thr Asn Val Ser
1               5                   10                  15

Tyr Gln Glu Thr Thr Thr Pro Ser Thr Leu Gly Ser Thr Ser Leu His
            20                  25                  30

Pro Val Ser Gln His Gly Asn Glu Ala Thr Thr Asn Ile Thr Glu Thr
            35                  40                  45

Thr Val Lys Phe Thr Ser Thr Ser Val Ile Thr Ser Val Tyr Gly Asn
        50                  55                  60

Thr Asn Ser Ser Val Gln Ser Gln Thr Ser Val Ile Ser Thr Val Phe
65                  70                  75                  80

Thr Thr Pro Ala Asn Val Ser Thr Pro Glu Thr Thr Leu Lys Pro Ser
            85                  90                  95

Leu Ser Pro

<210> SEQ ID NO 9
<211> LENGTH: 179
<212> TYPE: PRT
<213> ORGANISM: homo sapiens

<400> SEQUENCE: 9

Glu Leu Pro Thr Gln Gly Thr Phe Ser Asn Val Ser Thr Asn Val Ser
1               5                   10                  15

Tyr Gln Glu Thr Thr Thr Pro Ser Thr Leu Gly Ser Thr Ser Leu His
            20                  25                  30

Pro Val Ser Gln His Gly Asn Glu Ala Thr Thr Asn Ile Thr Glu Thr
            35                  40                  45

Thr Val Lys Phe Thr Ser Thr Ser Val Ile Thr Ser Val Tyr Gly Asn
        50                  55                  60

Thr Asn Ser Ser Val Gln Ser Gln Thr Ser Val Ile Ser Thr Val Phe
65                  70                  75                  80

Thr Thr Pro Ala Asn Val Ser Thr Pro Glu Thr Thr Leu Lys Pro Ser
            85                  90                  95

Leu Ser Pro Gly Asn Val Ser Asp Leu Ser Thr Thr Ser Thr Ser Leu
            100                 105                 110

Ala Thr Ser Pro Thr Lys Pro Tyr Thr Ser Ser Pro Ile Leu Ser
            115                 120                 125

Asp Ile Lys Ala Glu Ile Lys Cys Ser Gly Ile Arg Glu Val Lys Leu
        130                 135                 140

Thr Gln Gly Ile Cys Leu Glu Gln Asn Lys Thr Ser Ser Cys Ala Glu
145                 150                 155                 160
```

-continued

Phe Lys Lys Asp Arg Gly Glu Gly Leu Ala Arg Val Leu Cys Gly Glu
                165                 170                 175

Glu Gln Ala

<210> SEQ ID NO 10
<211> LENGTH: 222
<212> TYPE: PRT
<213> ORGANISM: homo sapiens

<400> SEQUENCE: 10

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125

Glu Ala Asn His Val Asp Pro Cys Leu Pro Cys Thr Val Cys Glu Asp
    130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
        195                 200                 205

Gly Ser Ser Gln Pro Val Val Thr Arg Gly Thr Thr Asp Asn
    210                 215                 220

<210> SEQ ID NO 11
<211> LENGTH: 40
<212> TYPE: PRT
<213> ORGANISM: homo sapiens

<400> SEQUENCE: 11

Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
            20                  25                  30

Asp Lys Gln Asn Thr Val Cys Glu
        35                  40

<210> SEQ ID NO 12
<211> LENGTH: 42
<212> TYPE: PRT
<213> ORGANISM: homo sapiens

<400> SEQUENCE: 12

```
Glu Cys Pro Asp Gly Thr Tyr Ser Asp Glu Ala Asn His Val Asp Pro
1               5                   10                  15

Cys Leu Pro Cys Thr Val Cys Glu Asp Thr Glu Arg Gln Leu Arg Glu
                20                  25                  30

Cys Thr Arg Trp Ala Asp Ala Glu Cys Glu
            35                  40
```

<210> SEQ ID NO 13
<211> LENGTH: 120
<212> TYPE: PRT
<213> ORGANISM: homo sapiens

<400> SEQUENCE: 13

```
Arg Cys Ala Tyr Gly Tyr Tyr Gln Asp Glu Thr Thr Gly Arg Cys Glu
1               5                   10                  15

Ala Cys Arg Val Cys Glu Ala Gly Ser Gly Leu Val Phe Ser Cys Gln
                20                  25                  30

Asp Lys Gln Asn Thr Val Cys Glu Glu Cys Pro Asp Gly Thr Tyr Ser
            35                  40                  45

Asp Glu Ala Asn His Val Asp Pro Cys Leu Pro Cys Thr Val Cys Glu
        50                  55                  60

Asp Thr Glu Arg Gln Leu Arg Glu Cys Thr Arg Trp Ala Asp Ala Glu
65                  70                  75                  80

Cys Glu Glu Ile Pro Gly Arg Trp Ile Thr Arg Ser Thr Pro Pro Glu
                85                  90                  95

Gly Ser Asp Ser Thr Ala Pro Ser Thr Gln Glu Pro Glu Ala Pro Pro
            100                 105                 110

Glu Gln Asp Leu Ile Ala Ser Thr
        115                 120
```

<210> SEQ ID NO 14
<211> LENGTH: 162
<212> TYPE: PRT
<213> ORGANISM: homo sapiens

<400> SEQUENCE: 14

```
Pro Cys Leu Asp Ser Val Thr Phe Ser Asp Val Val Ser Ala Thr Glu
1               5                   10                  15

Pro Cys Lys Pro Cys Thr Glu Cys Val Gly Leu Gln Ser Met Ser Ala
                20                  25                  30

Pro Cys Val Glu Ala Asp Asp Ala Val Cys Arg Cys Ala Tyr Gly Tyr
            35                  40                  45

Tyr Gln Asp Glu Thr Thr Gly Arg Cys Glu Ala Cys Arg Val Cys Glu
        50                  55                  60

Ala Gly Ser Gly Leu Val Phe Ser Cys Gln Asp Lys Gln Asn Thr Val
65                  70                  75                  80

Cys Glu Glu Cys Pro Asp Gly Thr Tyr Ser Asp Glu Ala Asn His Val
                85                  90                  95

Asp Pro Cys Leu Pro Cys Thr Val Cys Glu Asp Thr Glu Arg Gln Leu
            100                 105                 110

Arg Glu Cys Thr Arg Trp Ala Asp Ala Glu Cys Glu Glu Ile Pro Gly
        115                 120                 125

Arg Trp Ile Thr Arg Ser Thr Pro Pro Glu Gly Ser Asp Ser Thr Ala
        130                 135                 140
```

-continued

```
Pro Ser Thr Gln Glu Pro Glu Ala Pro Pro Glu Gln Asp Leu Ile Ala
145                 150                 155                 160
Ser Thr
```

CHIMERIC ANTIGEN RECEPTORS

In a first aspect, the present invention relates to chimeric antigen receptors (CAR) composed of at least an extracellular domain, a transmembrane domain and an intracellular domain, the extracellular domain comprises a spacer domain located C-terminally to a ligand-binding-domain also present in the extracellular domain, whereby the spacer domain comprises at least part of the CD34 molecule. Further, the present invention relates to the nucleic acid molecule encoding the same as well as vectors and cells containing the same. The cells include engineered T-cells and NK-cells and derivatives thereof. Further, the present invention relates to a pharmaceutical composition comprising the CAR e.g. in form of a vector, a polynucleotide encoding the CAR or the CAR itself and, in addition, cells, cell lines or host cells accordingly. The CAR according to the present invention is useful in adoptive cell therapy. Finally, a method for enrichment or purification of CAR, in particular, of genetically engineered cells, cell lines or host cells expressing the CAR according to the present invention is provided.

PRIOR ART

The idea of exploiting the immune system to target e.g. cancer cells is not new and already well documented in the 19th century, when William Coley repeatedly inoculated live bacteria into malignant skin tumors of patients, with the idea to thereby stimulate the immune system to recognize and kill the tumor cells. Today, immunotherapies against cancers can be divided into three divergent but complementing strategies. Active immunotherapies enhance the patient's immune system to provoke an active immune response, leading to recognition of tumor-associated antigens and elimination of the malignant cells. Passive immunotherapies induce immune responses by administration of exogenously produced components such as lymphocytes and antibodies. Modulatory immunotherapies are thought to amplify endogenous immune responses against cancer cells by general enhancement of the responsiveness of the immune system. Active immunotherapy can involve either polyvalent vaccines that are derived from whole tumor cells and/or dendritic cells or antigen-specific vaccines.

T-cells are the best characterized effector cells mediating specific immunity against malignant or virus-infected cells. T-cells recognize specific antigens on target cells via their T-cell receptor (TCR) however only in association with HLA class I or class II. An important factor to understand the failure of autologous T-cells to recognize and destroy the malignant cells in cancer patients is the process of T-cell development in the thymus. A huge variety of T-cell receptors (TCR) capable of binding to antigens is created by V(D)J recombination of germ-line DNA in T-cell precursors and will be capable of recognizing (almost) any antigen that is present in the body or can be introduced by pathogens. However, natural thymic positive and negative selection processes in humans lead to the loss of >>95% of these T-cells and only permits the survival of autologous T-cells that express TCRs with low or no affinity towards endogenous antigens. This natural selection severely dampens/limits the ability of the patient's immune system to detect the HLA-restricted endogenous antigens that are often expressed on cancer cells. Therefore, genetic engineering of T-cells (and also NK-cells) to stably express activating receptors against selected tumor-associated antigens is an attractive approach to overcome these problems.

Strategies to broaden the adoptive cell therapy (ACT) concentrated on the development of autologous T-cells genetically engineered to express tumor-specific antigen receptors, so these cells can efficiently recognize and kill malignant cells. A summary of adoptive therapy of cancer with CAR redirected T-cells is provided e.g. in Hombach et al., Current Molecular Medicine, 2013, 13(1), 1-10. Therein, the CAR effects are summarized including co-stimulation activity as well as improvement and prolongation of the redirected anti-tumor T-cell response. In addition, the adverse effects of this kind of adoptive therapy are described including "cytokine storm" and "T-cell repression". These antigen receptors can be classical T-cell receptors (TCRs) or chimeric antigen receptors (CARs) where single-chain antibody fragments (scFv) are fused with the cytoplasmic part of TCR ζ-chain (Dotti G, et al., Immunol Rev. 2014; 257(1): 107-26 and Schamel W W, Reth M. Curr Opin Biotechnol 2012; 23(5):780-4.

While transgenic TCRs only recognize antigens/epitopes presented by MHC molecules, the major advantage of CARs is that they recognize the surface antigens on target cells in a non-MHC-restricted manner. The first generation of CARs did not include co-stimulatory signals such as CD28, 4-1BB, OX40 or 2B4 and in the majority of trials demonstrated no clear clinical benefits in patients. However, efficient target recognition and profound activation of the transgenic T-cells with specific and efficient killing of antigen-positive cells was achieved with $2^{nd}$ generation CARs that included one co-stimulatory domain. Third generation CARs carry two co-stimulatory domains, thus providing three signals for the cell after binding of the CAR to the specific antigen peptide, but have not been used widely in research or clinical studies.

Most CARs are composed of the heavy and light chain of a monoclonal antibody scFv and co-stimulatory and different TCR signaling domains (see e.g Dotti G, et al., Immunol Rev. 2014; 257(1):107-26.

Here, a hinge aka spacer region links the antigen-recognizing domain of the scFv and the transmembrane and signaling cytoplasmic domains in the CAR constructs. Commonly, the constant CH2CH3 domain of IgG1 or IgG4 hinge regions were used due to the flexibility, lack of immunogenicity and easy adaptable modifications of the length (Guest R D, et al, J Immunother. 2005; 28(3):203-11). Also, quick detection of the CARs with these domains on the surface of transduced T-cells in combination with rapid enrichment procedures (MACS) made this spacer region attractive. Other authors successfully employed a hinge region based on human CD8 (e.g. for CD19 CARs). In comparison, the CD8 hinge is a rather short amino acid sequence and the spatial distance between the CAR and the target epitope in relation to the target cell membrane can be an activity-limiting factor. Another disadvantage is that identification and enrichment of transduced T-cells with monoclonal antibodies against the CD8 hinge region is not readily possible, as CD8 is naturally present on T-suppressor cells. In 2010, Hombach et al., Gene Ther. 2010; 17(10):1206-13, demonstrated that the IgG1 CH2CH3 spacer region is activated by cells that express either the FcγRI (CD64) or the FcγRII (CD32) Fc receptors. This unintended but specific activation followed by killing of the Fc receptor-positive cells was independent of the fact whether the targeted antigen structure was or was not present on the target cells. In 2015, Hudecek et al. demonstrated also for the IgG4 CH2CH3 domain that binding to CD32 and CD64 induces activation signals that leads to killing of cells independent from the presence of the CAR target antigen (Hudecek M, et al., Cancer Immunol Res. 2015; 3(2):125-35). Additionally, the authors demonstrated in vivo in mice with human T-cells, that Fc receptor-positive cells in the lungs of the animals activated the CAR transgenic T-cells. These activated T-cells then quickly disappeared in the animals due to activation-induced cell death. Importantly, these CAR-transduced T-cells failed to protect the animals from the CD19+ leukemic cells that were the intended target cells for the CARs. To prevent this loss of anti-tumor activity/specificity of the CAR positive T-cells in vivo in the presence of Fc receptor-positive cells, both groups introduced a few amino acid substitutions that prevent binding of these CH2CH3 domains to Fc receptors.

Recently, chimeric antigen receptors comprising an extracellular spacer which comprises at least part of the extracellular domain of the human low-affinity growth factor (LNGFR also known as NGFR or CD271) or a derivative thereof, are described in WO 2016/042461 A1. It is identified therein, that allegedly CARs containing the LNGFR as a spacer domain thereby substituting the known hinge CH2CH3 Fc domain allows to reduce any off-target immune responses and are not prematurely cleared by the host immune system. In addition, it is identified therein that transduced T-cells can be selected and tracked based on the LNGFR spaced constructs.

Rationale to Use a CD19 CAR for Initial Proof of Principle

In the last 5 years, human studies using CARs against the CD19 antigen which is uniformly present on all B-cell malignancies except plasma cell malignancies, and engineered TCRs against MAGE-A3 have demonstrated the huge therapeutic potential of these re-directed T-cells in patients where all other therapy approaches had ultimately failed. As even a single dose of re-infused T-cells can survive and expand for extended periods of time in the recipients, clinical cure of some malignancies has been achieved for months and years. After the initial proof of concept studies pioneered by Carl June and his colleagues for CD19+ leukemias (Porter D L, et al., N Engl J Med. 2011; 365(8):725-33) and six months event-free survival rate of 67% and an overall survival rate of 78% in these heavily pre-treated patients with refractory ALL, more than 100 investigational new drug applications (INDs) for CAR- and TCR-modified T-cells have been issued in the USA, with approximately ⅓ targeting CD19 on B-cell leukemias and lymphomas. Other important target antigen structures on malignant B-cells that are currently CD20 and CD22, both also (almost) B-cell lineage specific antigens.

However, administering genetically engineered T-cells was also associated with toxic side effects and even mortality (Porter DL, et al., N Engl J Med. 2011; 365(8): 725-33 and Linette GP, et al., Blood 2013; 122(6):863-71). Only second and third generation CAR constructs include co-stimulatory domains that will mediate maximum activation of the T-cell after engagement of the CAR. Therefore, in addition to the complete elimination of all leukemic cells, important on-target/off-tumor toxicities of B-cell lineage-specific CARs e.g. against CD19, CD20 and CD22 are the ablation of normal CD19/CD22/CD20+ B-cells, for as long as the genetically engineered T-cells are present. This side effect of B-cell lineage specific CARs leads to decreased immunoglobulin serum levels that can partially be compensated for by regular infusions of immunoglobulins. Interestingly, CD20 CARs also recognize a small proportion of malignant melanoma cells where CD20 is expressed. Elimination of this subpopulation of primitive cells is sufficient to induce remission in a fraction of these patients. In July 2016, the FDA stopped a Juno Therapeutics CD19 CAR phase I/II trial, after three deaths occurred in patients under 30 years of age with CD19+ malignant cells. Prior to the infusion of transduced autologous T-cells, these three patients had received chemotherapy with cyclophosphamide and fludarabine for mild lymphodepletion and in order to booster the engraftment of transduced cells (www.fiercebiotech.com/biotech/fda-halts-juno-car-t-trial-after-three-patient-deaths).

The CD34 antibody QBend10 is utilized in the CliniMACS device from Miltenyi Biotec GmbH, Germany. This antibody binds to the class II epitope in CD34, which is resistant to neuraminidase but sensitive to glycoprotease. The antibody binding site in CD34 was mapped as being present within a region of 16 amino acids by Philip et al., Blood 2014; 124(8):1277-87. Specifically, this 16 amino acid region containing the epitope of the QBend10 antibody is located between positions 42 to 57 in human CD34, see also SEQ ID. No. 2 corresponding to the CD34 protein encoded by the sequence of NM 001773.2 and the codon optimized nucleic acid sequence of Seq. ID No. 1.

In WO 2013/153391 A1 a polypeptide useful in adoptive cell therapy has been described. The epitope of the QBend10 antibody was inserted in a polypeptide framed by rituximab binding epitopes whereby these rituximab binding epitopes represent a suicide epitope. Therein, the polypeptide with the QBend10 binding epitope framed by the rituximab binding epitopes have been added to a transfer vector which co-expresses e.g. a CAR molecule via a T2A site. Thus, this polypeptide should allow on the one hand selecting cells which are identified as expressing the QBend10 binding epitope while on the other side, these cells allow for suicide due to the rituximab binding epitopes.

Miltenyi Biotec GmbH, Germany, provides clinically approved magnetic beads based systems allowing enrichment or purification of specific cell types based on antigen antibody binding whereby the antibody is bound to the magnetic or parametric particles accordingly. Thus, automated cell labelling and enrichment is possible.

Production of genetically engineered cells for adaptive cell therapy, typically, T-cells or NK-cells, are performed by transfecting or transducing said cells with appropriate means including plasmids, vectors like viral vectors etc. After transfection or transduction, these cells are cultured for selection of the desired cells accordingly. Typically, the selection is based on known selection systems including usage of resistance genes (e.g. neomycin or puromycin, see Fehse B. et al. Blood. 2004; 104(10):3408-9.) or enrichment by expression of MACS-selectable special proteins on the cell surface e.g. truncated CD34, truncated CD19, truncated EGFR or similar, see e.g Philip et al., see above, Di Stasi et al., N Engl J Med. 2011; 365(18):1673-83. (CD19), and Wang X, et al. 2011; 118(5):1255-63 EGFR.

However, these techniques require some time to generate/grow the respective cells including long-term cultivation. That is, the transduction of human blood lymphocytes is effected by standard techniques including cultivation and selection based on e.g. antibiotic resistance accordingly. However, there is still a need for improved CAR molecules and cells expressing the same, in particular, in view of immunogenicity and fast availability.

BRIEF DESCRIPTION OF THE PRESENT INVENTION

In a first aspect, the present invention relates to a chimeric antigen receptor (CAR) composed of at least the following domains:
an extracellular domain, a transmembrane domain and an intracellular domain whereby the extracellular domain comprises a ligand-binding-domain, like an antigen-binding-domain, and a spacer domain C-terminal to the ligand-binding-domain and whereby the spacer domain comprises at least part of the CD34 molecule. In particular, the CAR is a CAR molecule wherein the spacer domain comprises at least one of the sequences of SEQ ID Nos. 5, 6, 7, 8 or a sequence at least 90% identical thereto. In an embodiment, the spacer domain consists of the above sequences. Further the present invention relates to a polynucleotide encoding the CAR according to the present invention, a vector comprising said polynucleotide as well as a cell, cell line or host cell containing the vector or containing a nucleic acid molecule according to the present invention or expressing the CAR molecule according to the present invention accordingly.

In addition, an embodiment of the present invention relates to a pharmaceutical composition comprising the CAR as defined herein as well as a polynucleotide encoding the same or a vector containing said polynucleotide.

In addition, a CAR is provided suitable in adoptive cell therapy. Further, it has been recognized that using at least part of the CD34 molecule as a hinge region in the production of a CAR molecule has beneficial effects.

Further, a therapeutic method, namely adoptive transfer of genetically modified cells is provided using the cells or CAR molecule according to the present invention. Of course, the method for treating and/or preventing a disease in a subject may also be conducted with the vector containing the nucleotide sequence encoding said CAR molecule accordingly. That is, a method for treating e.g. cancer or other diseases involving an immune response against cells, like cancer cells, based on the CAR molecule according to the present invention is provided.

BRIEF DESCRIPTION OF THE DRAWINGS

As shown in FIGS. 6A and 6B, no lysis of MOLM14 cells occurred as it is the case for the non-virus transduced T-cells while a effector/target cell ratio-dependent lysis can be seen for the CAR expressing primary T-cells with CD123F, CD123J and CD33.

DETAILED DESCRIPTION OF THE PRESENT INVENTION

Figure 1:
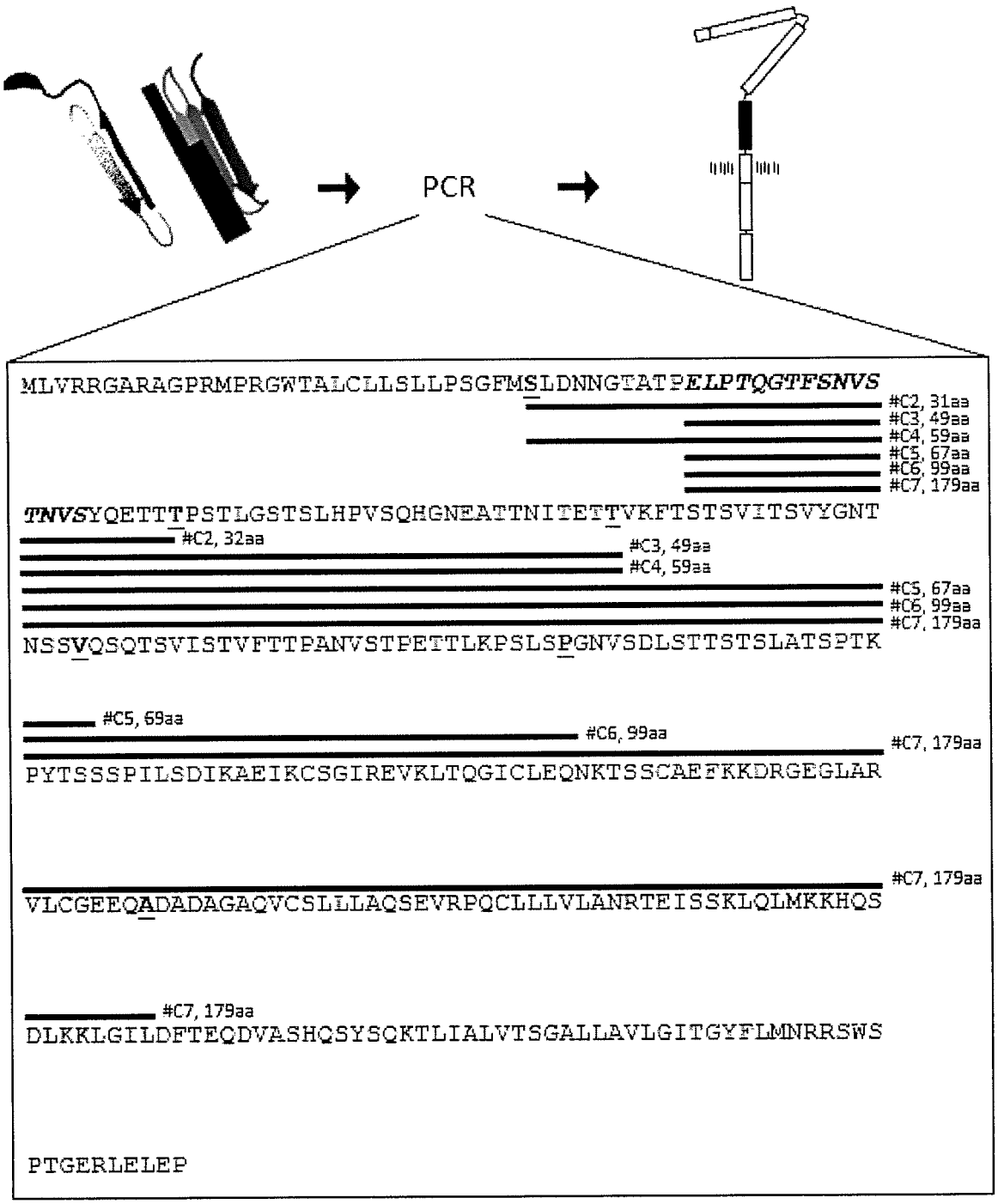
FIG. 1 is a schematic overview of the CD34 spacer sequences used according to the present invention. Codon-optimized cDNA sequences were used to allow further incorporation into the desired CAR molecules with suitable restriction enzyme sites. SEQ ID NO: 2 is shown in this Figure.

In a first aspect, the present invention relates to a chimeric antigen receptor (CAR) composed of at least the following domains:

an extracellular domain, a transmembrane domain and an intracellular domain whereby the extracellular domain comprises a ligand-binding-domain, like an antigen-binding-domain, and a spacer domain C-terminal to the lingand-binding-domain and whereby the spacer domain comprises at least part of the CD34 molecule.

The term "intracellular domain" is used interchangeably with the term "cytoplasmic domain" unless otherwise identified.

In this connection, the term "chimeric antigen receptor" or "CAR" or "CARs" as used herein refers to engineered receptors which can confer an antigen specificity onto cells. Further, this term also includes embodiments that the specificity may not rely on antigen-antibody level but on a ligand-receptor-binding-level. That is, the chimeric antigen receptor include molecules wherein the antigen specificity is not based on an antigen-antibody interaction but refers to a ligand-receptor-interaction accordingly. For example, suitable ligand-receptor-interaction includes the interaction of cytokine/cytokine receptor interaction but also other ligand receptor interactions known in the art. In a specific embodiment, the CARs of the invention comprise an antigen specific targeting region, an extracellular domain, a transmembrane domain, optionally one or more costimulatory domains and an intracellular signaling domain.

The "antigen specific targeting domain" present in a chimeric antigen receptor provides the CAR with the ability to bind to the target antigen of interest. Typically, the antigen specific targeting domain is a protein or peptide having the ability to recognize and bind to a molecule, typically a cell surface molecule present on the cell surface of the target cells. The target cell is e.g. a tumor cell. Illustrative antigen specific targeting domains include antibodies or antibody fragments or derivatives, extracellular domains or receptor, ligands for cell surface molecules/receptors, or receptor binding domains thereof, and tumor binding proteins.

In an embodiment of the present invention, the antigen specific targeting domain is or is derived from an antibody, examples include the variable regent (FV), a complementary determining region (CDR), a FAB, a single-chain antibody (scFv), a heavy chain variable region (H), a light chain variable region (VL) and a carmelite antibody (VHH). Most of the CARs presently described in the art contain a single chain antibody as the antigen specific targeting domain. Depending on the cell type said scFv may be murine, human or humanized scFv.

Examples of antigens which may be targeted by the CAR of the invention include but are not limited to antigens expressed on cancer cells and antigen expressed on cells associate with various other diseases or conditions including hematologic diseases, autoimmune diseases, inflammatory diseases and infectious diseases.

The skilled person is well aware of selecting a suitable targeting domain depending on the target, e.g. the type of cancer to be treated. The antigen specific targeting domain according to the present invention is prepared by known techniques.

As noted above, the CAR of the present invention may also comprise one or more co-stimulatory domains. These domain may enhance cell appropriation, cell survival and development of the same. The skilled person is well aware of suitable domains including co-stimulatory signal domains derived from CD28, CD34 (OX40) or CD137 (4-1BB). These co-stimulatory domains may be provided alone or in combinations thereof, for example as described in third generation CAR molecules. An overview about the CAR molecules is provided e.g. in Gilham D. E. et al., trans in molecular Medcine, 2012, 18(7), 377-384.

Further, the CAR according to the present invention comprises intracellular signaling domains. These domains may transduce the effector function signal and direct the cell to perform its specialized function. The signaling domain also known as being part of the endodomain, intracellular domain or cytoplasmic domain may comprise a CD3 zeta or Fc epsilon receptor, (IgE receptor) gamma chain, signaling chain and/or a costimulatory domain. Suitable signaling domains are described in the art accordingly. For example, the intracellular domain contains a CD28 signaling domain, in particular, a CD28 domain lacking the lck binding motif. Daneben ICOS, 4-1BB, NKp44/DAP12, NKG2D/DAP10, 2B4/LAT, NTB-A, DNAM-1, NKp80, IL-33R/, IL-1RAcP, ckit, MyD88, IRAK, TRAF6.

The CAR of the invention may also comprise a transmembrane domain. The transmembrane domain is typically a transmembrane sequence from any protein which has a transmembrane domain. Preferred embodiments thereof include the zeta chain of a T-cell receptor, the transmembrane domain derived from CD28 or derived from CD8a.

That is, the CAR according to the present invention is composed of at least the domains being an extracellular domain also known as ectodomain and a spacer domain, a transmembrane domain and the intracellular domain. The extracellular domain includes a spacer domain being located C-terminally to the ligand binding domain present in the extracellular part of the CAR molecule. According to the present invention, the spacer domain consists or comprises of at least a part of the CD34 molecule.

As used herein, the term "at least a part of the CD34 molecule" refers to a fragment of the CD34 molecule allowing immune selection. This part of the CD34 molecule is e.g. an epitope of an antibody having a length of at least 6, like at least 7 linear amino acids. In case of conformational epitopes, the size of the peptide is larger. In an embodiment of the present invention, the at least part of the CD34 molecule refers to a peptide of at least 6 consecutive amino acids of SEQ ID No. 2.

The ligand binding domain including the antigen binding domain present in the chimeric antigen receptor according to the present invention is spaced apart from the transmembrane domain by the presence of the spacer domain. This spacer domain links the antigen or ligand binding domain to the transmembrane domain and should be flexible enough to allow the antigen or ligand binding domain to orient in different directions to facilitate antigen or ligand recognition.

As used herein, the term "comprise" or "comprising" as well as the terms "contain" or "containing" includes the embodiments of "consist" or "consisting".

In an embodiment, the spacer domain comprising at least part of the CD34 molecule is located between the ligand binding domain, like the antigen binding domain, and the transmembrane domain.

The spacer domain comprising at least part of the CD34 molecule confer properties to the CARs such it as allows for immune selection of cells expressing said CAR. In particular, the spacer domain allows for the selection of systems like the CliniMacs Prodigy System of Miltenyi Biotec Germany based on Macs Selection. The CAR of the present invention is preferably suitable for facilitating immune selection of cells transduced with the CAR according to the present invention. Further, the CAR of the present invention avoids activation of unwanted and potentially toxic off-target immune responses and allows CAR expressing cells including T-cells and NK-cells to persist in vivo without being prematurely cleared by the host system. Further, the CAR of the present invention support purification of the transduced or transfected cells expressing the CAR in the presence of cells expressing the antigen or receptor of which the CAR is designed. That is, the CAR of the present invention mediate therapeutically significant effects including anti-cancer effects against cancer the CAR is designed to target.

It is clear to the skilled person that beside the specifically identified sequences of protein of peptides and nucleotides, the present invention also contemplates the use of derivatives and fragments thereof. In this connection the term derivative as used therein refers in so far as it refers to proteins or polypeptides to include substitutions of, variations of, modification of, replacement of, deletion of, and/or addition of one (or more) amino acid residues from or to the sequence providing that the result in protein or polypeptides retains the desired function. The skilled person is well aware of determining suitable derivatives and fragments based on the teaching available in the prior art accordingly.

In a further embodiment, the spacer domain comprises at least the amino acid sequence of Seq. ID No. 3 of the CD34 molecule.

The CD34 molecule as used herein refers to the CD34 molecule as described in under gene bank excession No. NM_01773.2 whereby the sequence of Seq. ID No. 1 represents a codon optimized sequence derived therefrom.

In a further embodiment, the spacer domain comprise at least one of the sequence of Seq. ID Nos. 4, 5, 6, 7, 8 or 9 or a sequence at least 90% identical thereto. That is, a homolog having a sequence homology of at least 90%.

Unless otherwise defined, the terms "homology" and "identity" as well as "homolog" and "identical" are used interchangeably herein. Homology refers to the magnitude of identity between two sequences. Homolog sequences have the same or similar characteristics, in particular, have the same or similar property of the sequence as identified. As noted, the homologue has at least 90% identity with the sequences mentioned, homology is at least 90%, like 95%, 96%, 97%, 98%, 99% of the amino acid sequence it is referred to.

In a further embodiment, the CAR according to the present invention is a CAR wherein in spacer domain is an amino acid sequence comprising Seq. ID No. 3, like comprising any one of SEQ ID No. 4, 5, 6, 7 or 8, but not containing the C-terminus of the CD34 molecule starting from amino acid 221 of Seq. ID No. 2. It has been recognized by the present inventors that the presence of the C-terminus amino acid sequences reduces the possibility to enrich or select the appropriate cells expressing the CAR accordingly.

That is, the present inventors recognized that substituting the known spacer domain also known as hinge region typically composed of the CH2CH3 domain of IgG antibodies present in CAR molecules with the at least part of the CD34 molecule allows to enrich and select easily transduced cells expressing the desired CAR based on the CD34 expression and, in addition, allows to remain the cytotoxic activity of the transduced cells accordingly without any side effects described for the CH2CH3 hinge region in the prior art.

Thus, in an embodiment of the present invention, the CAR is a CAR comprising at least the following domains starting on the N-terminus to the C-terminus:
  i) an antibody domain;
  ii) an extracellular spacer domain according to the present invention,
  iii) a transmembrane domain;
  iv) a cytoplasmatic domain comprising a) optionally at least one costimulatory domain and comprising b) an intracellular signaling domain.

In an embodiment of the present invention, the CAR is a CAR molecule wherein the transmembrane domain comprises one or more of (i) a transmembrane domain of a zeta chain of a T-cell receptor, CD28, CD8a, and/or (ii) the intracellular domain contains a CD28 signaling domain, in particular, a CD28 domain lacking the lck binding motif, and/or (iii) the intracellular domain contains a CD3 zeta or Fc epsilon receptor I gamma-signaling chain and/or a costimulatory domain.

In another embodiment, the present invention relates to a polynucleotide encoding the CAR molecule according to the present invention. The polynucleotides of the invention may comprise DNA or RNA structures as well as other structures known to the skilled person accordingly. The polynucleotides may be single-stranded or double-stranded. Due to the genetic degeneracy, numerous different polynucleotides can encode the same polypeptide accordingly. The polynucleotides used in the present invention may codon optimized. The skilled person is well aware of suitable means and method allowing codon optimization. For example, the sequence of these CD34 molecule as shown in SEQ ID No. 1 represents a codon optimized CD34 encoding nucleic acid sequence. By altering the codons in the sequence, they are tailored to match with a relative abundance of corresponding tRNAs, thus, increasing expression as well as having an additional degree of translation control.

Further, the present invention provides vectors comprising the polynucleotide according to the present invention, for example, the vector is a viral vector. In an embodiment of the present invention, the vector is a self-inactivating viral vector containing a suicide gene.

Generally, a vector is a tool allowing or facilitating the transfer of an entity from one environment to another. Typically, vectors are used in recombinant nucleic acid techniques allowing transfer of nucleic acid sequences into environments, like target cells. Vectors can be non-viral or viral vectors including plasmids, RNA molecules, artificial chromosomes and viruses. Of course, the vector may be a nicked nucleic acid but also include embodiments wherein the nucleic acid sequences are present with nanoparticles for introducing the same into the target. The vectors used in the present invention may be plasmid, mRNA or virus vectors and may include a promotor for the expression of a polynucleotide and optionally a regulator of the promotor. In addition, in an embodiment, the vector includes a self-inactivating mechanism for example including a suicide gene. A suitable example of such a vector on the basis of a lentiviral vector is disclosed in Roellecke, K., et al, Gene Therapy, 2016, 1 to 12.

In an embodiment of the present invention, the lentiviral vector described therein is used. The vector is introduced into the cells by transfection or transduction systems. Typical transfection methods include electroporation, DNA biolistics, lipid-mediated transfection, liposomes, immuneliposomes, lipofectin, cationic agent mediated transfection and combinations thereof.

In case of using viral vector, including retro-viral vector, lentiviral vectors may be used. Lentiviral vectors are able to infect both dividing and non-dividing cells. As mentioned, a suitable lentiviral vector including a suicide gene is described by Roellecke, K., et al, see above.

In a further embodiment, cell, cell line or host cell are provided containing the vector according to the present invention or a nucleic acid molecule according to the present invention, or expressing the CAR according to the present invention. The cells are typically genetically engineered cells comprising and stably expressing the CAR of the invention.

In this connection, the term "genetically engineered" refers to a cell being manipulated by genetic engineering. That is, the cells contain a heterologous sequence which does not naturally occur in said cells. Typically, the heterologous sequence is introduced via a vector system or other means for introducing nucleic acid molecules including liposomes. The heterologous nucleic acid molecule may be integrated into the genome of said cells or may be present extra-chromosomally, e.g. in the form of plasmids. The term also includes embodiments of introducing genetically engineered, isolated CAR polypeptides or CAR molecules into the cell.

In an embodiment of the present invention, the cells, cell lines or host cells are T-cells or T-cell derived cells including naive T-cells, memory T-cells, central memory T-cells, vector cells but also natural killer cells and other hematopoietic stem cells or other cells capable of giving rise to therapeutically relevant progeny. It is contemplated that the cells, in particular, the T-cells and NK-cells, include progenitor cells accordingly. In an embodiment, the genetically engineered cells are autologous cells. In case of T-cells, the T-cells may be a mixed population of CD4 positive and CD8 positive T-cells or may be separated population of these types of T-cells. In an embodiment, the population is obtained from a single clone.

After transfection or transduction of the cells, the cells are cultured as known in the art, for example, including any kind of stimulating compounds.

In an embodiment of the present invention, these cells are enriched or selected based on the expression of the part of CD34 present in the CAR molecule.

That is, a further embodiment of the present invention relates to a method for purifying or isolating genetically engineered cells, genetically engineered cell lines or genetically engineered host cells expressing a CAR molecule according to the present invention, in particular, genetically engineered T-cells or NK-cells comprising the step of selecting the cells, cell lines or host cells based on the expression of the extracellular spacer domain comprising at least part of CD34.

It has been recognized by the present inventors that the use of at least part of CD34 as a spacer domain in the extracellular part of the CAR molecule allows to enrich easily transduced cells expressing CAR molecules. In addition, it has been recognized that substituting the at present commonly used hinge region of CH2CH3 with the at least part of CD34 component reduces the adverse effects of said CH2CH3 hinge region. In addition, earlier and easier selection of transduced or transfected cells are possible. Moreover, since the CD34 molecule is usually not present on mature cells, an adverse interaction should not occur.

As used herein, the terms "enrichment", "depletion", "selection", "isolation" or "purification" are used interchangeably unless otherwise identified. A suitable means for enabling enrichment or purification is the system of Miltenyi Biotec GmbH, Germany, based on the MACS technology. That is, the magnetic based separation e.g. using the CliniMACS prodigy system of Miltenyi Biotec enables quick and easy but safe isolation of transduced cells which can be used thereafter in adoptive cell therapy.

The applicability of the MACS system, e.g. obtainable from Miltenyi Biotec, has been shown before in WO 2013/153391 as well as in the publication of Roellecke et al, Gene Therapy, 2016, 1 to 12.

By using the method according to the present invention, long-term cultivation for selection of suitable transduced cell lines can be avoided. In particular, it is possible to efficiently enrich/select genetically modified cells including T-cells with different CARs in so far as they include the at least part of CD34 in an extracellular domain, by MACS. It is possible to utilize a clinically approved CD34 selection kit e.g. from Miltenyi Biotec, to provide the transduced cells for adoptive therapy. In particular in case of autologous adoptive cell therapy, the method according to the present allows to reduce the preparation time for these cells accordingly.

In a further aspect, the present invention relates to therapeutic methods and pharmaceutical compositions containing and based on the CAR of the present invention. That is, herein are provided methods for treating a disease associated with the ligand or antigen targeted by the CAR of the invention in a subject in need thereof. The method comprises administering an effective amount of the CAR, a polypeptide or a vector encoding the CAR, or a cell, cell line or host cell expressing said CAR to a subject in need thereof so as to treat the disease associated with the ligand or antigen in the subject. The skilled person is well aware of suitable treatment methods including the way of administration, the dosage etc.

The pharmaceutical composition according to the present invention is a composition that comprises or consists of a therapeutically effective amount of the pharmaceutically active agent. In an embodiment, the pharmaceutical composition includes further a pharmaceutically extracellular carrier, diluent or excipient or combinations thereof. These carriers, diluents or excipients are known to a skilled person and the choice thereof depends on the intended route of administration. The pharmaceutical composition may comprise further additional compounds including binders, lubricants, suspending agents, coating agents or solubilizing agents. These agents are known to the skilled person accordingly.

In an embodiment, the pharmaceutical composition is a composition containing transduced or transfected cells, like transduced or transfected T-cells or transduced or transfected NK-cells for use in adoptive cell therapy in a subject in need thereof. In addition, the method of treatment according to the present invention may include administration of transduced or transfected cells as mentioned before.

The present invention will be described further by way of examples without limiting the invention thereto.

Examples

For the following example, the basic principle is to include antibody binding sites of ΔCD34 or ΔNGFR as hinge/spacer region in CARs, thereby replacing the CH2CH3 domain of 233 amino acids derived from human IgG with sequences of codon-optimized ΔCD34 or ΔNGFR. Ideally, these replacements would allow normal signaling of CARs upon binding of the specific antigens by the scFv parts of the CARs and at the same time facilitate enrichment of the transduced T-cells by MACS technology without unspecific activation or other detrimental effects. Choosing a segment of ΔCD34 or ΔNGFR as a hinge region would have the huge advantage that directly labeled anti-bodies for magnetic sorting of the transduced cells are available for GMP applications.

Figure 2:
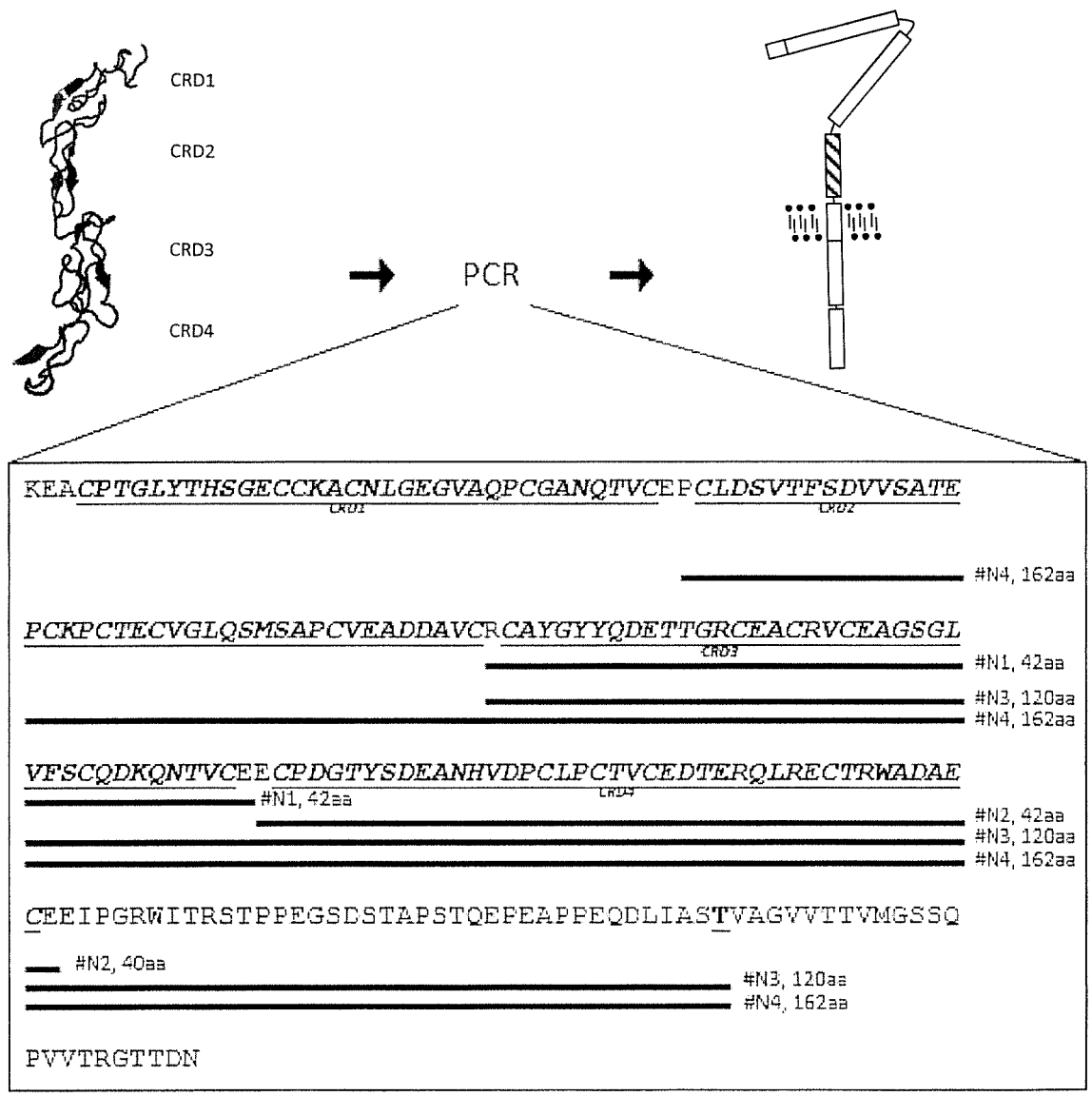
FIG. 2 is a schematic overview of the NGFR/CD271 included as cDNA sequences into the CAR molecules as described. SEQ ID NO: 10 is shown in this Figure.

The CD34 antibody QBend10 is utilized in the CliniMACS device from Miltenyi. This antibody binds to the class II epitope in CD34, which is resistant to neuraminidase but sensitive to glycoprotease. The antibody binding site in CD34 was mapped as a region of 16 amino acids by Philip et al., see above. For ΔNGFR/CD271, the epitope recognized by the CD271 antibody in the Milteny Biotec GmbH GMP-selection kit for the CliniMACS device is located somewhere within the third or fourth cysteine-rich repeats of the NGFR molecule. We therefore created several deletion mutants as shown in FIG. 2. For the initial testing, we decided to determine the functionality of these two novel spacers in the context of a well-established and functional CD19 CAR construct, for which we kindly obtained the sequence from Claudia Rössig, see Rossig C, et al., Klin Padiatr. 2005; 217(6):351-6. We then designed and bought a human codon usage-optimized sequence for this CAR from GeneArt, Regensburg, Germany. Ultimately, the final spacer as defined in the following analyses was also validated in the context of other CARs targeting different antigen structures on myeloid cells.

CD34 Spacers (#C1-#C7)

Figure 3A:
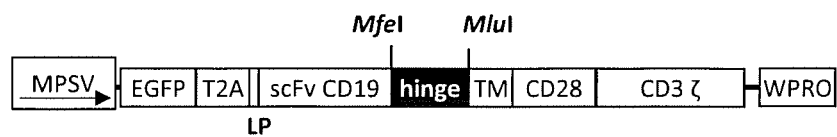
FIG. 3 A.) shows a scheme of the expression cassette with the lentiviral vector used herein. EGFP and the CD19 CAR were driven by the MPSV U3 promotor and co-expressed via a T2A site. The spacer domains were exchanged using the restriction sites Mfe I and Mlu I.
FIG. 3B.) FACS analysis of Jurkat cells transduced with the lentiviral vector with a protein expression cassette shown in A.).

Philip et al. described the epitope of the QBend10 antibody, which is the antibody clone used for the kit microbead selection by Miltenyi Biotec, as a stretch of 16 amino acids at the positions 42-57 in human CD34. However, it was not possible to include this minimal sequence, which we called #C1, as a spacer into the Mfe I-Mlu I restriction enzyme sites of the human codon optimized CD19 CAR construct (FIG. 3), as none of ten ligations with appropriate DNA oligos resulted in a stable CD19 CAR DNA construct. Therefore, we systematically added, guided by 3-dimensional modeling of CD34, additional amino acid stretches of CD34 3' and 5' to this 16 amino acid core sequence in various length (6 variants in total, #C2-#C7) into our CD19 CAR construct as codon-optimized sequence linker into the Mfe I-Mlu I restriction enzyme sites of the CD19 CAR (FIG. 1).

NFGR Spacers (#N1-N4).

We have also designed a spacer for the CD19 CAR based on our codon-optimized truncated ΔNGFR sequence, see Seq. ID No. 10 as described in Roellecke et at. (Gene Therapy, 2016, see above). Although the exact binding epitope of the ME20.4 CD271 antibody from Miltenyi was not known, we hypothesized that it would bind within the 3rd or 4th cysteine-rich domain (CRD) of the surface portion. Therefore, we designed 4 spacer do-mains (#N1-#N4) containing either the 3rd, the 4th or both CRDs of the surface domain of NGFR for the inclusion in the CD19 CAR between the Mfe I and Mlu I restriction enzyme sites, see also FIG. 2

All constructs developed in this application are listed in the following table 1:

| No. | CD34 | aa position* Seq. ID. No. | NGFR/ CD271 | aa position** Seq. ID. No. |
|---|---|---|---|---|
| 1 | #C1 | 42-57, 3 | #N1 | 108-147 11 |
| 2 | #C2 | 32-63 4 | #N2 | 148-189 12 |
| 3 | #C3 | 42-90 5 | #N3 | 108-227 13 |
| 4 | #C4 | 32-90 6 | #N4 | 65-227 14 |
| 5 | #C5 | 42-110 7 | | |
| 6 | #C6 | 42-140 8 | | |
| 7 | #C7 | 42-220 9 | | |

Amino acid position relative to the start (+1, methionine) of CD34* or NGFR**

Antibody Staining Analyzed by Flow Cytometry

Figure 3B:
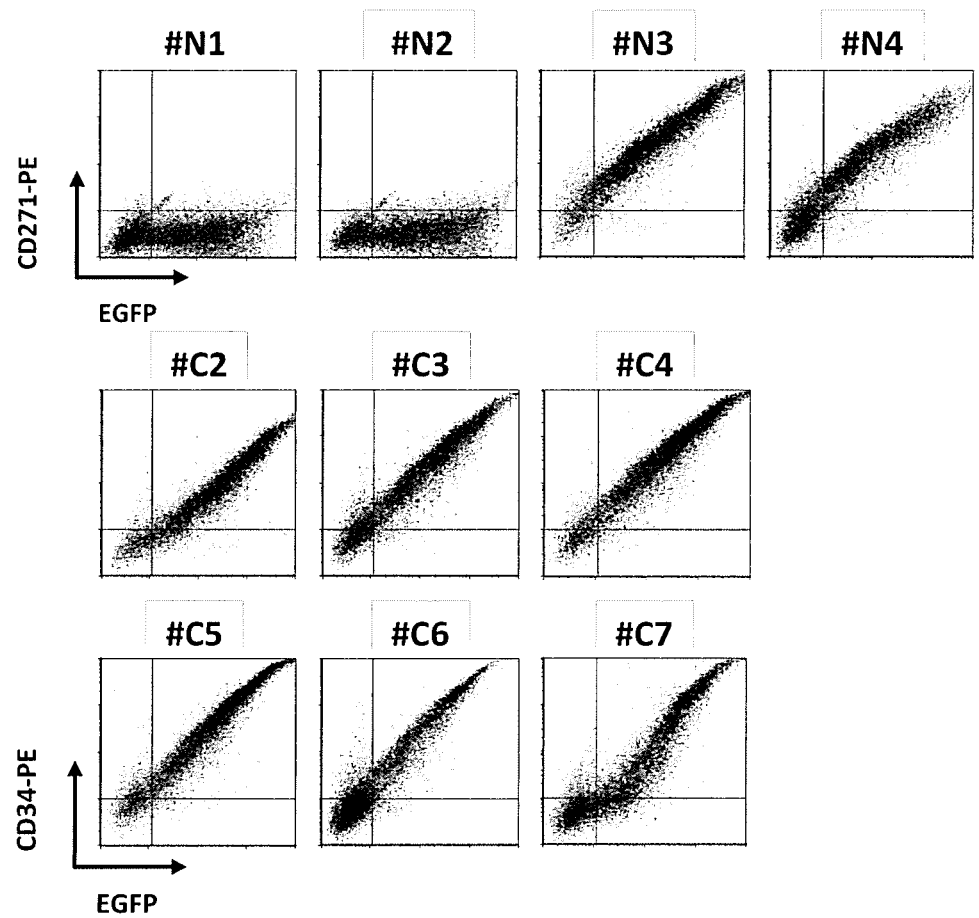

First, we tested whether the corresponding fluorescently labeled monoclonal antibodies for CD34 and NGFR from Miltenyi GmbH were able to recognize the novel spacer domains in the context of the CD19 CAR. To this end, the T-cell line Jurkat cells were lentivirally transduced with vectors co-expressing the CD19CAR with the modified spacers and EGFP as marker for positive transduction (FIG. 3). Transduced Jurkat cells were grown for 4 days and subsequently stained with the CD34 monoclonal antibody QBend10 or the CD271 monoclonal antibody ME20.4. Importantly, as shown in FIG. 3B, CD19 CARs with the spacer domain comprised out of the $3^{rd}$ or $4^{th}$ CRD (#N1, #N2) were not stainable with the ME20.4 antibody, although EGFP expression clearly indicated positive transduction of the Jurkat cells. T-cells transduced with CD19 CARs whose spacers comprising longer regions of NGFR, #N3 and #N4, were readily stained and there was a clear direct correlation between the positivity for EGFP and for NGFR. In contrast, all CD19 CAR constructs carrying the QBend10 epitope with surrounding amino acids from CD34 (#C2-#C7) were successfully stained with the QBend10 antibody. Therefore, for further testing, we concentrated on the following eight spacers: #N3-4 and #C2-C7.

MACS Selection

Although antibody staining followed by flow analysis indicates the successful binding of an antibody to its epitope, it still needs to be determined whether the binding was stable enough for forces occurring during MACS enrichment. Therefore, Jurkat cells transduced with LV vectors coexpressing EGFP and the CD19 CARs with the spacers #02-7 and #N3-4 were used for MACS selection using directly beads-labeled antibodies. Samples were collected from the transduced Jurkat cells prior to the MACS columns (before column), from the flow-through of the columns after one round of selection (flow-through=negative selection) and also from the eluates obtained from the columns after release of the cells bound in the columns (eluate=positive selection). Samples were analyzed after staining with the HPCA2 (CD34 epitope I) or the ME20.4 monoclonal antibodies and analyzed by flow cytometry.

Surprisingly, positive selection of Jurkat cells expressing either the construct #N3 or the longer construct #N4 did not work well at all: although there was a clear enrichment of strongly positive cells (eluate), the numbers were minute, as the vast majority of transduced cells did not remain in the columns but was passing through the columns and therefore was lost for selection purposes. This is clear from the overlay comparing the three fractions. Numerically, the percentages of positive cells only decreased from 60.1±2.6% (Before MACS) to 57.2±1.8% (flow through) for #N3 and 51.4±11.5% (Before MACS) to 49.7±11.7% (flow through) for #N4.

A similar loss of transduced cells was also observed for Jurkat cells transduced with EGFP and CD19 CAR containing #02, the shortest amino acid stretch of CD34 that was tested for enrichment by MACS: compare 68.7±2.7% to 68.1±3.0%. By increasing the length of the CD34 aa stretches, increasingly less transduced Jurkat cells were passing through the column: compare 61.6±2.7% to 47.6±2.1% (#C3), 64.3±25.3% to 47.0±6.3% (#C4), 65.5±2.1% to 41.1±5.0% (#C5) and 50.7±10.5% to 28.3±6.8% (#C6). However, this was different for construct #07 which had 80 aa more than #C6. Here, the percent of positive Jurkat cells in the flow through increased again: 78.4±3.2% vs. 67.1±3.5%.

These experiments in Jurkat cells clearly indicated that the ΔNGFR-derived linker region where the CD271 antibody binds is not suitable for inclusion as selection tool in a CAR. In contrast, the CD34 regions #6 and to a lower degree also #7 appeared very promising.

Figure 4:
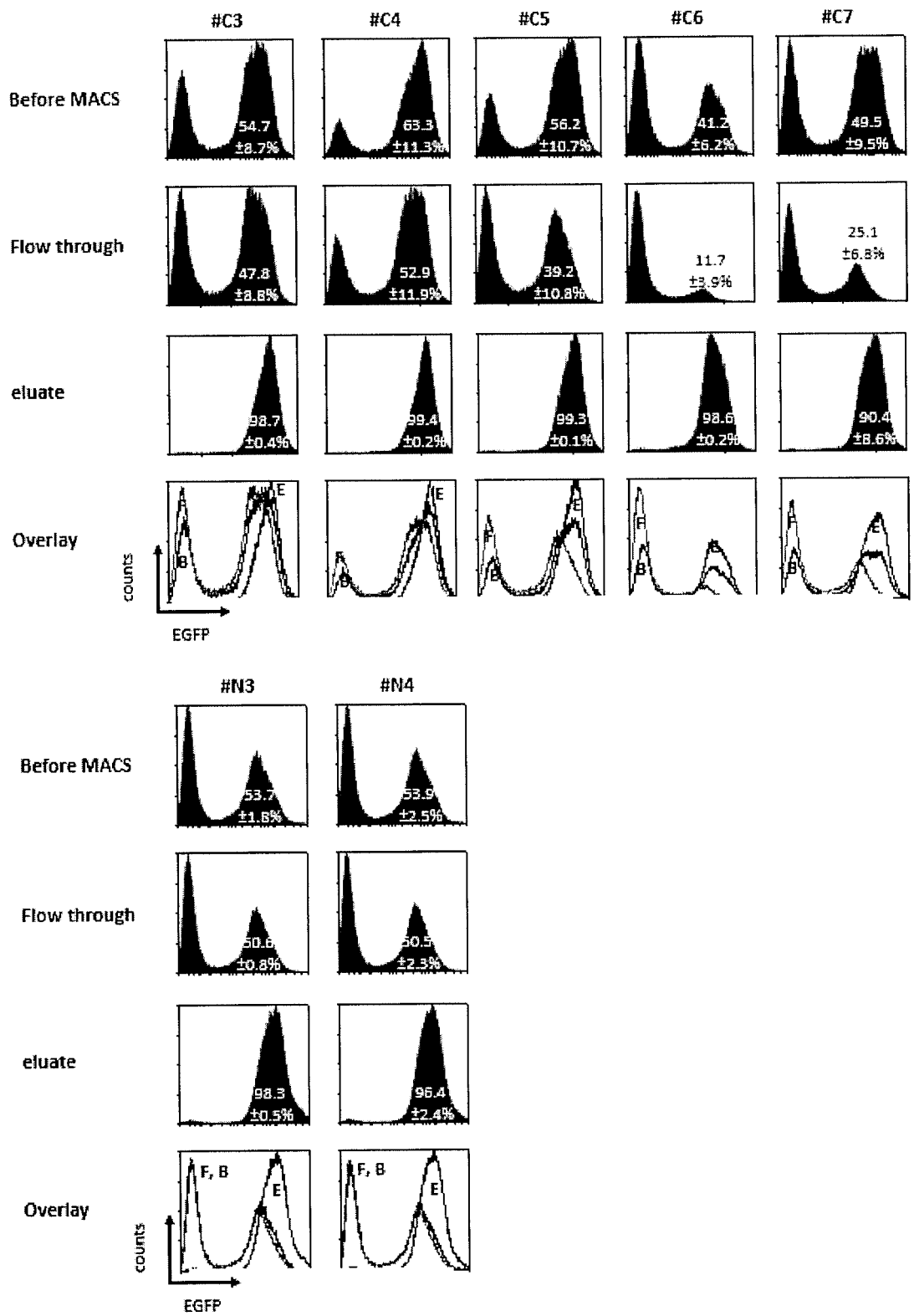
FIG. 4 shows a MAC selection of primary T-cells using the expression cassette with the lentiviral vector shown in FIG. 3A. CD19 CAR transduced T-cells were collected before MACS columns were applied from the flow through and from the eluate when performing MACS separation. The overlay shows the data before MACS, flow through and eluate Representative histograms are shown. Mean±S.E.M. are calculated from at least three independent experiments.

These results were confirmed with primary human T-cells that were transduced with CD19 CAR constructs with #C2-7 or #N3-4 spacer regions and then three days later used for MACS selection (FIG. 4). The CAR with the #C6 linker clearly facilitated the best enrichment with less positive T-cells in the flow through (41.2±6.2% versus 11.7±3.9%). Second best suited for enrichment was the CD19 CAR with the #C7 linker. Use of the #C3-5 and #N3-4 linker regions in the CD19 CAR resulted in efficient enrichment of transduced human T-cells, but was also associated with the loss of the majority of cells in the flow through of the columns.

Cytotoxicity Assay and PK Toxicity

After determining that the CD19 CAR construct with the #C6 linker region from CD34 worked best for selection in the MACS device upon staining with a directly labeled monoclonal antibody, we next assessed whether the cytotoxicity of the CD19 CAR is also preserved in the CD19 CAR #C6 construct. We also tested whether inclusion of the hCYP4B1P+12 suicide gene as a second transgene in our lentiviral vector allowed efficient in vitro control of CD19 CAR #C6 expressing primary human T-cells with the prodrug *perilla* ketone (PK), see also Roellecke et. al., Gene Therapy 2016. Thus, two different CD19 CAR lentiviral vectors—either with the IgG4 CH2CH3 or the #06 linker region—were cloned. In these vectors, the hCYP4B1P+12 suicide gene replaced the EGFP cDNA (see the EGFP CD19 CAR #C6 vector in FIG. 3A).

Figure 5A:
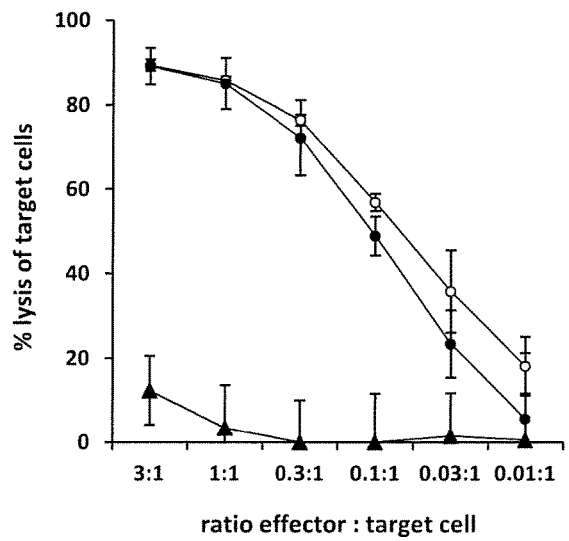
FIGS. 5A and 5B shows cytotoxicity and suicide of transduced primary T-cells. T-cells separated with the MACS enrichment system were tested for their cytotoxicity and suicide accessibility. T-cells transduced with the expression cassette described above either containing the IgG4 CH2CH3 or the CD34 #C6 as hinge domains as well as non-transduced T-cells were incubated with CD19 positive REH cells overnight. A.) The survival of the REH cells was assessed after PI staining for live/dead discrimination by FACS analysis. For each construct, mean±S.E.M. from at least three experiments is shown. B.) T-cells used for the REH cytotoxicity assay in A.) were incubated for 24 h with increasing concentrations of PK and cell survival was analyzed by flow cytometry. For each construct, mean±S.E.M. from at least three experiments is shown.

Primary human T-cells were transduced with the two VSV-G pseudotyped lentiviral vectors similarly as previously described (Roellecke et al., 2016). After three days, transduced cells were then MACS enriched by staining either with CD34 labeled MACS beads or with biotinylated Fab polyclonal antibodies followed by streptavidin MACS beads. Cells were then incubated with cells from the CD19 positive ALL cell line REH overnight in different effector to target cell ratios without the supplement of IL-2. The following day, the cultures were harvested, PI stained and analyzed by FACS. As shown in FIG. 5A, non-transduced primary T-cells cultured for the same time under identical conditions only induced very weak cytotoxicity at high effector to target cell ratio (3:1). T-cells expressing the previously described CD19 CAR with the IgG4 CH2CH3 as spacer domain efficiently killed the CD19 positive REH cells as expected. Importantly, T-cells expression the CD19 CAR #C6 killed the CD19 positive target cells equally efficient, e.g. killing of 56.8±2.1% (#C6) and 48.9±4.6% (CH2CH3) REH cells at 0.1:1 effector to target cell ratios. Remarkably, there is no statistical difference between the two CD19 CARs with distinct spacer domains demonstrating the feasibility and efficacy of #C6 to serve as an alternative linker region in the CD19 CAR.

Figure 5B:
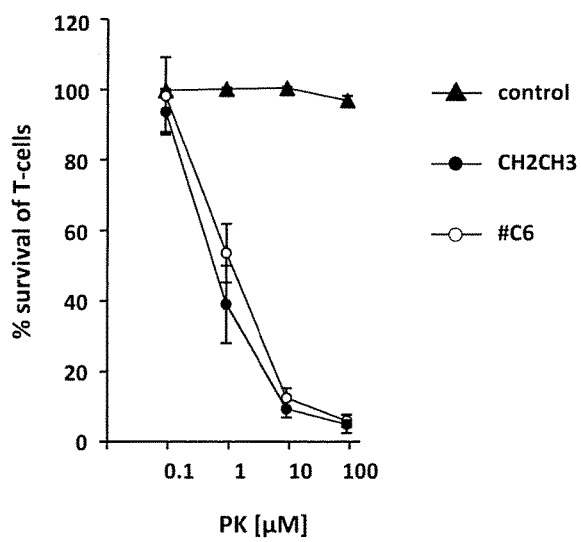

Next, we tested whether the MACS enriched primary T-cells that killed the REH cells can still be efficiently killed/controlled by hCYP4B1P+12 by exposure to *perilla* ketone as prodrug. To this end, the T-cells used for the cytotoxicity assay were incubated with increasing concentrations of PK and after 24 h T-cell survival analyzed by FACS. Non-transduced T-cells displayed no toxicity towards PK, whereas transduced T-cells rapidly died upon PK incubation (FIG. 5B). Also here was no difference between the two CARs (with CH2CH3 and #C6 linkers) observed. Similar observations on the cytotoxic activities were observed for other CARs containing any one of the other linker shown in table 1. For example, similar to FIG. 5A, FIG. 7 shows the results of the CAR molecules with the CH2CH§ and the #3 linkers, respectively. As demonstrated, the lysis is similar to the CH2CH§ linker and the #6 linker shown in FIG. 5A.

Confirming the CD34 #C6 Hinge Domain as Functional in Other CARS

Figure 6A:
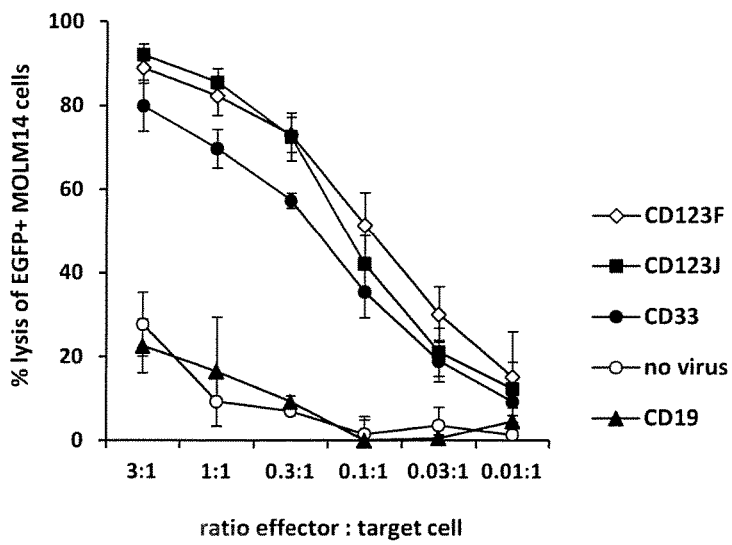
FIGS. 6A and 6B demonstrates specificity of the cytotoxic activity of transduced primary T-cells expressing different CARs, namely CD19, CD33 or CD123 CARs. T-cells transduced with lentiviral vectors containing expression cassettes similar to the expression cassette shown in FIG. 3 A.) with CD19, CD33 and CD123 CARs with a C6 spacer domain targeting either CD33 or CD123 or MOLM14 cells were incubated overnight with the AML cells. The next day, survival of MOLM14 cells was assessed by PI staining for live/dead discrimination by flow cytometry analysis. B) As a control, cells with no virus and CD19 have been used since CD19 is not expressed on the MOLM14 cells.
Figure 6B:
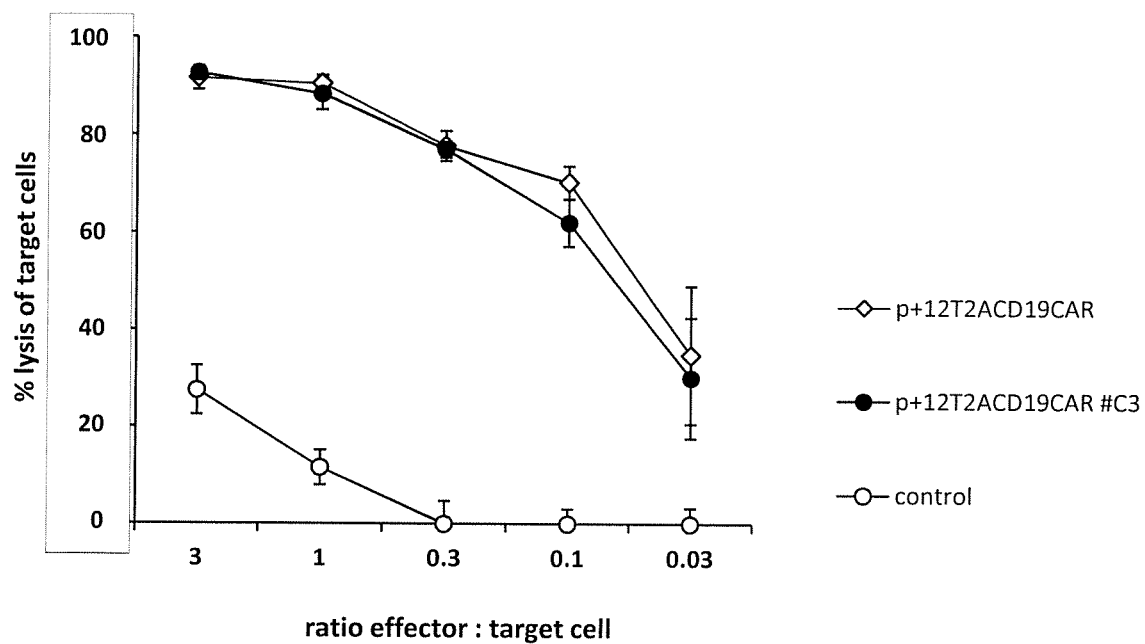

Finally, we wanted to confirm that the #C6 fragment of CD34 is also functioning well as hinge region in other CARs. We therefore designed and bought codon-optimized cDNAs for three single chains fragments, two CD123/IL3 and one CD33, from GeneArt, Regenburg, and cloned these sequences into the EcoRV-MfeI restriction enzyme sites of the CD19 CAR #C6 construct that also contains hCYP4B1. Primary human T-cells were then transduced with four different lentiviral vectors expressing the CD123J, the CD123F, the CD33 and the CD19 CAR cDNAs. Four days later, transduced T-cells were enriched with CD34 microbeads by MACS and then incubated with cells from the MOLM14 cell line overnight. MOLM14 cells are CD33+ CD123+CD19− acute myeloid cells from the M5 subtype with a FLT3 internal tandem duplication (ITD) that have been previously used for cytotoxicity studies with CD33 and CD123 CARs. As shown in FIGS. 6A and 6B, transduced and MACS-enriched T-cells expressing the CD123F, the CD123J or the CD33 CARs efficiently killed the MOLM14 cells after overnight incubation at effector to target cell ratios of 1:10 or even lower lower. In contrast, the same T-cells expressing a CD19 CAR or the same T-cells not transduced at all showed little toxicity against the MOLM14 leukemia cells only at higher effector/target cell ratios. Therefore, these results demonstrate that the #06 hinge/spacer domain is also functioning for MACS selection in other CARs and fully functional for the cytotoxic activity of CAR constructs.

In conclusion, we have developed here a new hinge region or spacer domain for CAR molecules exampled by the a region of 99 amino acids, called #C6, located asymmetrically around the binding site of the monoclonal antibody QBEND10 in human CD34 that can be included as hinge/spacer domain in different CARs and does not negatively affect the cytotoxic activity of the CARs. Importantly, the codon-optimized #06 amino acid sequence can be used to efficiently enrich/select genetically modified T-cells with different CARs by MACS. It will therefore allow to readily enrich for transgene positive T-cells and also other immune cells (e.g. NK cells) with clinically approved CD34 selection kits from Miltenyi Biotech.

However, as demonstrated above, the use of the at least part of the CD34 molecule in a CAR allows to purify efficiently the CAR expressing cells. Thus, it is possible to provide a tool for enrichment and purification of CAR molecules and cells expressing the same, in particular, with respect to adoptive cell therapy. As demonstrated, the cytotoxicity of the CAR molecules of table 1 is similar to the cytotoxicity of CAR molecules having other hinge regions, however, the advantage of the use of the hinge region according to the present invention is to enable easy and fast enrichment and purification further avoiding side-effects known for other hinge regions. This is not only true for the CAR molecule exemplified in the examples but for the CAR molecules and cells expressing e.g. the other constructs shown in table 1 accordingly. The CAR molecules according to the present invention in combination with the approved purification system of Miltenyi Biotech GmbH, Germany, namely, the CliniMACS system, allows to provide suitable cells for adoptive cell therapy, in particular, for treating cancer. Due to the universality of the CAR molecules depending on the ligand binding domain, in particular, the antigen binding domain in combination with the specific spacer domain according to the present invention, the CAR molecules represent a powerful tool for use in enrichment purification of transduced or transfected cells, in particular, T-cells useful in the treatment comprising adaptive cell therapy.

The invention claimed is:

1. A polynucleotide encoding a chimeric antigen receptor (CAR) composed of at least the following domains: an extracellular domain, a transmembrane domain and an intracellular domain, wherein the extracellular domain comprises a ligand-binding-domain and a spacer domain C-terminal to the ligand-binding-domain, wherein the spacer domain comprises a part of the CD34 molecule consisting of the amino acid sequence of SEQ ID NOS: 5, 6, 7, or 8 or a fragment of SEQ ID NO: 8, wherein the fragment contains at least the amino acid sequence of SEQ ID NO: 5, wherein the spacer domain is located between the ligand-binding domain and the transmembrane domain and wherein the spacer domain does not comprise any other part of the CD34 molecule.

2. A vector comprising the polynucleotide of claim 1.

3. The vector according to claim 2 being a self-inactivating viral vector containing a suicide gene.

4. The vector according to claim 2 being a viral vector.

5. A pharmaceutical composition comprising a vector according to claim 2.

6. An isolated cell containing a polynucleotide according to claim 1, containing a vector comprising said polynucleotide, or expressing a CAR encoded by the polynucleotide of claim 1.

7. A pharmaceutical composition comprising an isolated cell according to claim 6.

8. The isolated cell according to claim 6 being a T-cell or a NK-cell.

9. The polynucleotide according to claim 1 wherein the ligand-binding-domain is an antigen-binding-domain.

10. A pharmaceutical composition comprising a polynucleotide according to claim 1.

11. The polynucleotide according to claim 1 wherein (i) the transmembrane comprises a transmembrane domain of a zeta chain of a T-cell receptor, a CD28 transmembrane domain, or a CD8a transmembrane domain; and/or (ii) the intracellular domain contains a CD28 signaling domain, and/or (iii) the intracellular domain contains a CD3 zeta or Fc epsilon receptor I gamma signaling chain and/or a costimulatory domain.

12. The polynucleotide according to claim 11, wherein the intracellular domain contains a CD28 signaling domain lacking the lck binding motif.

13. The polynucleotide according to claim 1, wherein the part of the CD34 molecule being the only part of the CD34 molecule of the spacer domain has an N-terminus starting with amino acid 42 of SEQ ID NO: 1.

14. A method for purifying or isolating genetically engineered cells, cell lines or host cells expressing a CAR as defined in claim 1, comprising the step of selecting the cells, cell lines or host cells based on expression of at least part of the CD34 containing spacer domain.

15. The method according to claim 14 for purifying or isolating genetically engineered T-cells comprising the step of selecting T-cells based on the expression of the extracellular spacer domain.

16. A method for producing a CAR molecule as defined in claim 1 comprising the step of incorporating a spacer domain as defined in claim 1 into the CAR molecule.

17. A method for producing an isolated cell according to claim 6 comprising the step of incorporating at least a part of the CD34 molecule as a hinge region into the CAR molecule.

18. A polynucleotide encoding a CAR according to claim 1, the CAR comprising at least the following domains starting from the N-terminus to the C-terminus
   i) an antibody domain;
   ii) an extracellular spacer domain wherein the spacer domains comprises a part of the CD34 molecule consisting of the amino acid sequence of SEQ ID NOS: 5, 6, 7, or 8 or a fragment of SEQ ID NO: 8, wherein the fragment contains at least the amino acid sequence of SEQ ID NO: 5 and wherein the spacer domain does not comprise any other part of the CD34 molecule;
   iii) a transmembrane domain; and
   iv) a cytoplasmic domain comprising a) optionally at least one costimulatory domain and comprising b) an intracellular signaling domain.

19. A method of adoptive cell therapy of an individual comprising administering to said individual a therapeutically effective amount of an isolated cell according to claim 6.

20. The method according to claim 19 for the treatment of cancer.

* * * * *